(12) United States Patent
Fox, Jr. et al.

(10) Patent No.: US 7,690,558 B2
(45) Date of Patent: Apr. 6, 2010

(54) UTILIZING SCANNED SUPPLY INFORMATION AND A PATIENT TASK LIST TO DOCUMENT CARE

(75) Inventors: Charles S. Fox, Jr., Leawood, KS (US); Deborah J. Durrell, Kansas City, MO (US); Kris Kline, Kansas City, MO (US); Damon Herbst, Shawnee, KS (US)

(73) Assignee: Cerner Innovation, Inc., Overland Park, KS (US)

( * ) Notice: Subject to any disclaimer, the term of this patent is extended or adjusted under 35 U.S.C. 154(b) by 0 days.

(21) Appl. No.: 11/424,378

(22) Filed: Jun. 15, 2006

(65) Prior Publication Data

US 2007/0290028 A1    Dec. 20, 2007

Related U.S. Application Data

(63) Continuation-in-part of application No. 10/684,834, filed on Oct. 15, 2003.

(51) Int. Cl.
*G06F 17/00* (2006.01)
(52) U.S. Cl. .................. 235/375; 235/380; 235/382; 705/2; 700/86
(58) Field of Classification Search ............. 235/375, 235/380, 382, 382.5; 705/2; 700/86
See application file for complete search history.

(56) References Cited

U.S. PATENT DOCUMENTS

| | | | |
|---|---|---|---|
| 4,835,372 A * | 5/1989 | Gombrich et al. ............ 235/375 |
| 4,857,716 A | 8/1989 | Gombrich et al. |
| 5,153,827 A | 10/1992 | Coutre et al. |
| 5,317,506 A | 5/1994 | Coutre et al. |
| 5,594,786 A | 1/1997 | Chaco et al. |
| 5,781,442 A | 7/1998 | Engleson et al. |
| 6,519,569 B1 | 2/2003 | White et al. |
| 6,671,563 B1 | 12/2003 | Engleson et al. |
| 6,731,989 B2 | 5/2004 | Engleson et al. |
| 6,790,198 B1 | 9/2004 | White et al. |
| 6,915,170 B2 | 7/2005 | Engleson et al. |
| 6,985,870 B2 | 1/2006 | Martucci et al. |
| 7,096,072 B2 | 8/2006 | Engleson et al. |
| 7,103,419 B2 | 9/2006 | Engleson et al. |
| 7,107,106 B2 | 9/2006 | Engleson et al. |
| 7,117,041 B2 | 10/2006 | Engleson et al. |
| 2002/0147390 A1 * | 10/2002 | Markis et al. ............... 600/301 |
| 2002/0188467 A1 | 12/2002 | Eke |
| 2003/0009244 A1 * | 1/2003 | Engleson et al. .............. 700/86 |
| 2003/0139701 A1 | 7/2003 | White et al. |
| 2004/0243444 A1 * | 12/2004 | Steusloff et al. ............... 705/2 |

(Continued)

FOREIGN PATENT DOCUMENTS

WO     96/06944     5/1996

*Primary Examiner*—Allyson N Trail
(74) *Attorney, Agent, or Firm*—Shook, Hardy & Bacon L.L.P.

(57) ABSTRACT

A system and method in a computerized healthcare environment for determining whether one or more supply items are associated with one or more task items for a patient is provided. A patient identifier is received and patient data is accessed from the patient's electronic medical record. A scanned medical supply item identifier is received and data for the scanned supply item is accessed. The supply item data and patient data are utilized to determine whether one or more task items for the patient are associated with the scanned supply item.

22 Claims, 11 Drawing Sheets

U.S. PATENT DOCUMENTS

2004/0249673 A1 12/2004 Smith
2005/0086072 A1* 4/2005 Fox et al. .................. 705/2
2005/0107914 A1 5/2005 Engleson et al.
2005/0234778 A1 10/2005 Sperdutti

* cited by examiner

UTILIZING SCANNED SUPPLY INFORMATION AND A PATIENT TASK LIST TO DOCUMENT CARE

CROSS-REFERENCE TO RELATED APPLICATIONS

The present application is a continuation-in-part of co-pending U.S. application Ser. No. 10/684,834 filed Oct. 15, 2003, entitled TASK-BASED SYSTEM AND METHOD FOR MANAGING PATIENT CARE THROUGH AUTOMATED RECOGNITION. U.S. patent application Ser. No. 11/424,391, entitled "UPDATING FINANCIAL RECORDS TO REFLECT THE USE OF SUPPLY ITEMS FOR A PATIENT," filed on the same day as said application, and U.S. patent application Ser. No. 11/424,384 entitled "UPDATING SUPPLY INVENTORY DATA TO REFLECT THE USE OF A MEDICAL SUPPLY ITEM FOR A PATIENT," filed on the same day as said application.

STATEMENT REGARDING FEDERALLY SPONSORED RESEARCH OR DEVELOPMENT

Not applicable.

BACKGROUND

Hospitals and other clinical facilities face the task of managing the effective delivery of health services and accounting for supplies in a healthcare environment. Certain commercially available supply management information systems exist which may permit hospital administrators to select, purchase and monitor supplies and material for various operations. However, those platforms suffer from disadvantages of various types. Cost recovery on a patient basis, for instance to attempt to assign costs of supplies consumed during procedures performed for the patient can be difficult. Billing departments may be left with no alternative other than simply averaging costs of supplies over all patients, or assigning that clinical consumption to other cost centers within the organization. This may lead to cost distortions for insurance payments and other purposes.

Furthermore, in the commercially available supply management information systems, clinical supply consumption may be tracked or monitored, but only at a department or facility-wide level. For instance, a director of a surgical unit may be able to review how many scalpels or stents his or her unit consumed last month. However, these systems only permit the administrator to view and manage clinical supplies only at the aggregate level, without associating supply consumption to specific patients. As such, clinical administrators are not able to leverage the use of supply items for a particular patient in inventory records.

These commercially available supply management information systems also lack the ability to associate supply items with treatment of a patient. For example, they do not provide the ability to associate supply items with tasks or orders to be performed or that have been performed for a patient.

SUMMARY

In one embodiment, a method in a computerized healthcare environment for determining whether one or more supply items are associated with one or more task items for a patient is provided. A patient identifier to identify a patient is received and patient data is accessed from the patient's electronic medical record. A scanned medical supply item identifier identifying a non-pharmaceutical medical supply items is received and data for the scanned supply item is accessed. The supply item data and patient data are utilized to determine whether one or more task items for the patient are associated with the scanned supply item.

In another embodiment, a computerized system for determining whether one or more supply items is associated with one or more task items for a patient is provided. The system comprises a central information system containing patient data and supply item data, a patient identifier linking a patient to patient data in the central information system and a supply item identifier linking the non-pharmaceutical medical supply item to supply item data in the central information system. The system further comprises a portable information device for collecting the patient identifier and the supply item identifier and communicating with the central information system to access the patient data and supply item data.

In yet another embodiment, a method of retrieving and transmitting patient data in a computerized environment is provided. A patient identifier is retrieved with a portable information device, where the patient identifier identifies a patient. A supply item identifier is retrieved with a portable information device, where the supply item identifier identifies a non-pharmaceutical medical supply item. The patient identifier and the supply item identifier are transmitted to a central information system and current patient related information is received from the central information system at the portable information device.

BRIEF DESCRIPTION OF THE SEVERAL VIEWS OF THE DRAWINGS

The present invention is described in detail below with reference to the attached drawing figures, wherein.

DETAILED DESCRIPTION

Embodiments of the present invention are directed to a system and method for utilizing scanned supply information to create healthcare orders. Having briefly provided an overview of the present invention, embodiments of the invention will be discussed with reference to FIGS. 1-10.

Figure 1:
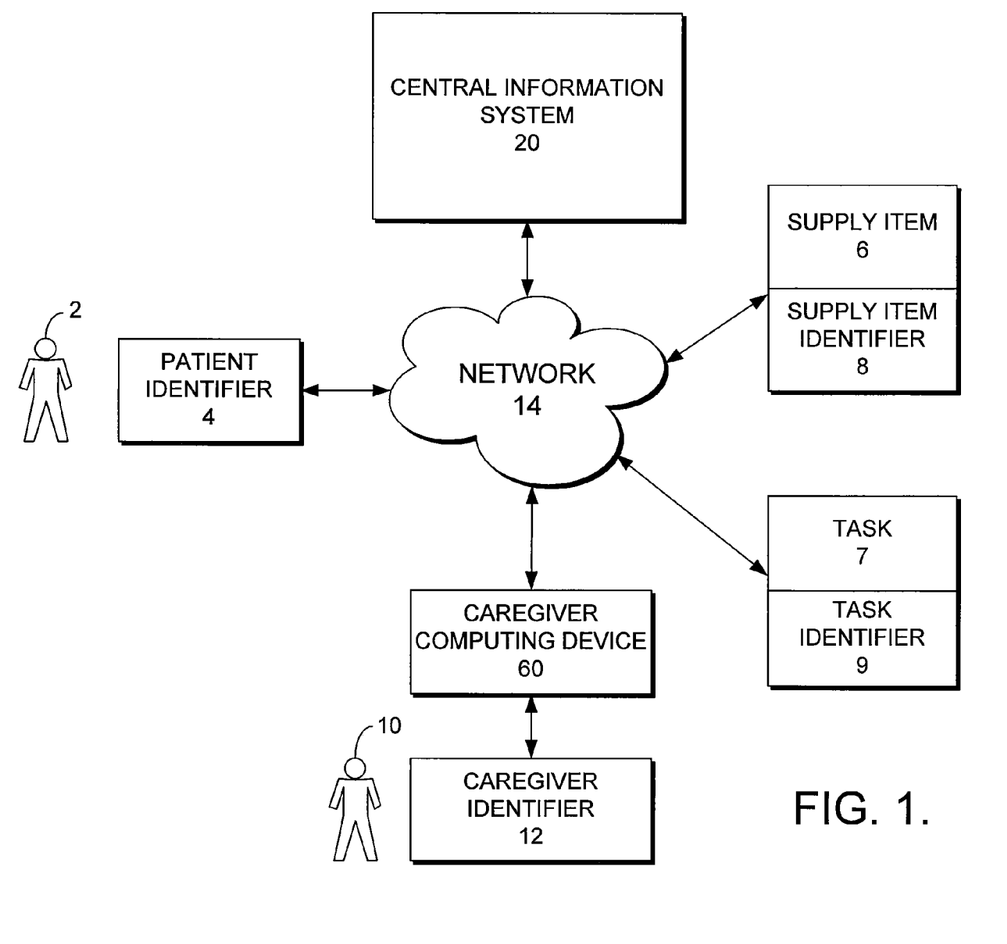
FIG. 1 is a block diagram illustrating components of a system for managing patient care in accordance with an embodiment of the invention.

Specifically, with initial reference to FIG. 1, a patient identifier 4 identifies a patient 2 and supply item identifier 8 may identify supply item 6. A caregiver identifier 12 identifies a caregiver 10. A task identifier 9 identifies a task 7. A central information system 20 and a caregiver computing device 60 are capable of communicating over a network 14. In an embodiment, the caregiver computing device is a portable, handheld computer. The caregiver computing device 60 is also capable of processing information associated with the patient identifier 4, the supply item identifier 8, the task identifier 9 and the caregiver identifier 12. The caregiver computing device 60 can transmit the information to the central information system 20. In this manner, each caregiver 10, each patient 2, each supply item 6 and each task 7 can be transmitted to the central information system 20. Although the components are shown as communicating over the network 14, peer-to-peer communication may also be possible. Each of the components of the system is described in greater detail below.

Figure 3:
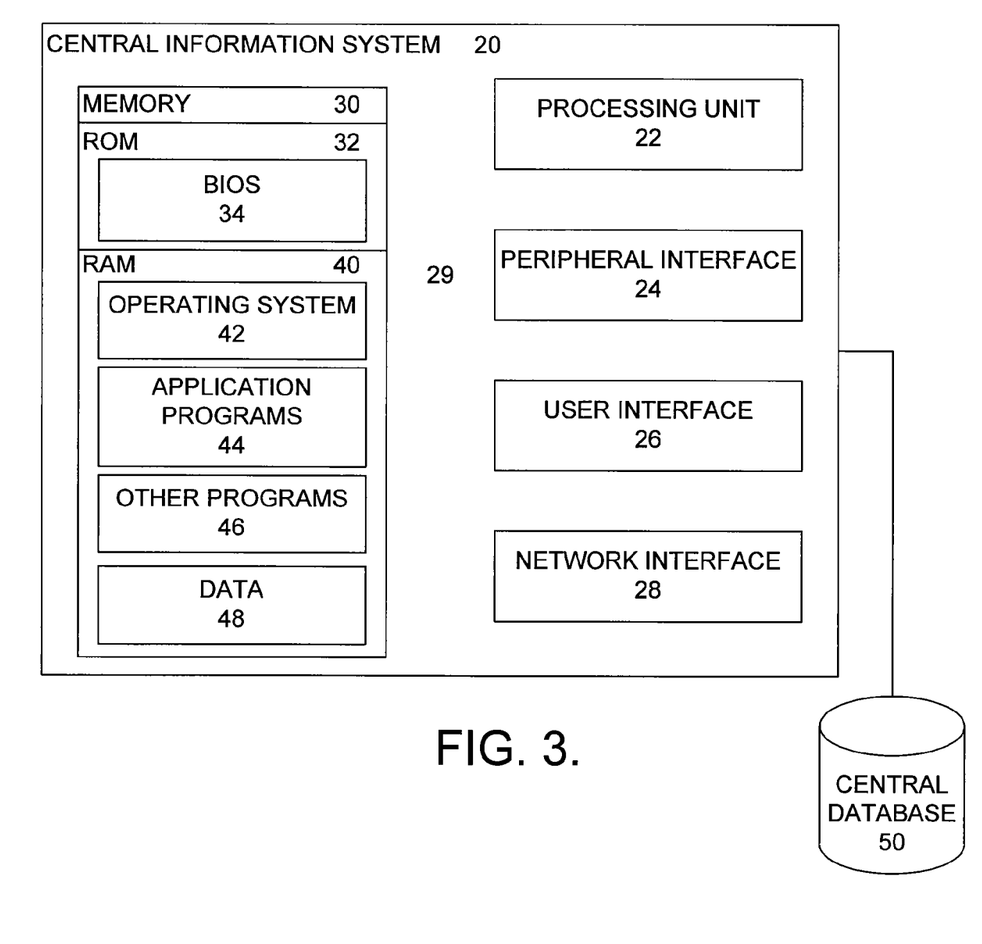
FIG. 3 is a block diagram illustrating components of a central information system in accordance with an embodiment of the present invention.

FIG. 3 illustrates an embodiment of the central information system 20. The central information system 20 may include a processing unit 22, a peripheral interface 24, a user interface 26, and a network interface 28. The central information system 20 may also include a memory 30. A system bus 29 couples the aforementioned components. The central information system 20 may also include or communicated with a central database 50.

The system memory 30 may include computer storage media in the form of volatile and/or nonvolatile memory such as read only memory (ROM) 32 and random access memory (RAM) 40. A basic input/output system 34 (BIOS), containing the basic routines that help to transfer information between elements within the central information system 20, such as during start-up, is typically stored in ROM 32. RAM 40 typically contains data and/or program modules that are immediately accessible to and/or presently being operated on by processing unit 22.

By way of example, and not limitation, FIG. 3 illustrates operating system 42, application programs 44, other program modules 46, and program data 48. The application programs 44 and other programs 46 may be described in the general context of computer-executable instructions, such as program modules, being executed by a computer. The applications programs 44 include components for matching patient data, caregiver data, and medication data in the central database 50 with identifiers transmitted by the caregiver computing device 60. Furthermore, the application programs 44 include components for generating a patient task list. The task lists are based upon knowledge databases in the central information system 20 that dictate a particular course of care. These tasks lists may be contained within the patient records 54 and the caregiver records 58 that are described below with reference to FIG. 4. Generally, program modules include routines, programs, objects, components, data structures, and the like that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, and the like.

The central information system 20 may also include other removable/non-removable, volatile/nonvolatile computer storage media. A hard disk drive may be provided that reads from or writes to non-removable, nonvolatile magnetic media, a magnetic disk drive that reads from or writes to a removable, nonvolatile magnetic disk, and an optical disk drive that reads from or writes to a removable, nonvolatile optical disk such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive is typically connected to the system bus through a non-removable memory interface and magnetic disk drive and optical disk drive are typically connected to the system bus by a removable memory interface.

A user may enter commands and information into the central information system through the user interface 26 using input devices such as a keyboard and pointing device, commonly referred to as a mouse, trackball or touch pad. Other input devices may include a microphone, satellite dish, scanner, or the like. These and other input devices are often connected to the processing unit 22 through the user input interface 26 that is coupled to the system bus 29, but may be connected by other interface and bus structures, such as a parallel port or a universal serial bus (USB). A monitor or other type of display device may also be connected to the system bus 29 via an interface, such as the peripheral interface 24. In addition to the monitor, computers may also include other peripheral output devices such as speakers and printer.

The illustrated central information system 20 is merely an example of a suitable environment for the system of the invention and is not intended to suggest any limitation as to the scope of use or functionality of the invention. Neither should the central information system 20 be interpreted as having any dependency or requirement relating to any one or combination of components illustrated.

The central information system 20 in the present invention will operate in a networked environment in conjunction with the network 14 as illustrated in FIG. 1, using logical connections to one or more remote computers, such as the caregiver computing device 60. As further described below, the caregiver computing device 60 may be a personal computer, and typically includes many of the elements described above relative to the central information system 20.

The network 14 may be the Internet and all components of the system may be accessible over the Internet. Logical connections for networking may include a local area network (LAN) or a wide area network (WAN), but may also include other networks. When used in a LAN networking environment, the central information system 20 may be connected to the LAN through the network interface 28 or adapter. When used in a WAN networking environment, the central information system 20 typically includes a modem or other means for establishing communications, such as the Internet. The modem, which may be internal or external, may be connected to the system bus 29 via the user input interface 26, or other appropriate mechanism.

Figure 4:
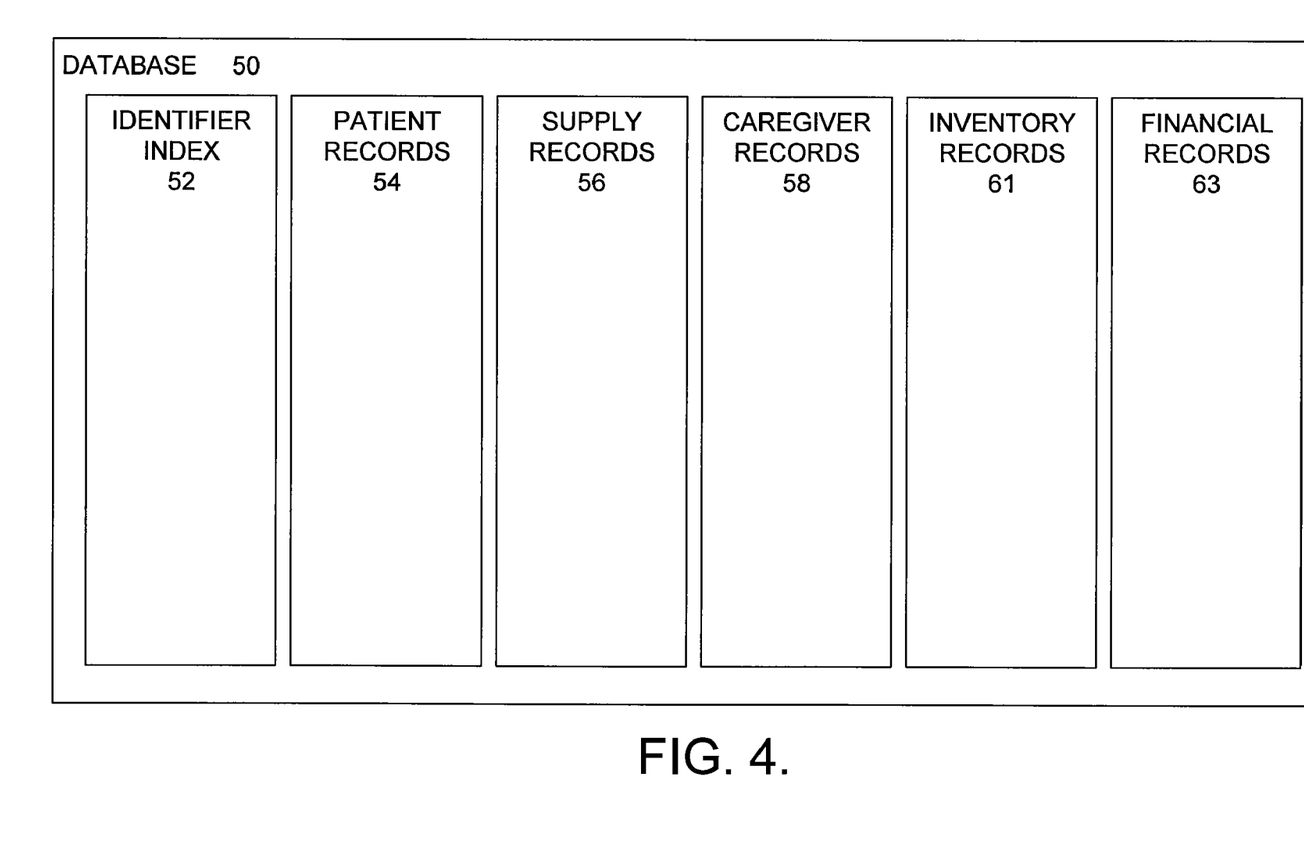
FIG. 4 is a block diagram illustrating a central database of the central information system in accordance with an embodiment of the present invention.

FIG. 4 illustrates an embodiment of the central database 50. The central database 50 may include an identifier index 52 linking the identifiers to all of the identified patients, supply items, inventory, financial records, and caregivers. In the illustrated embodiment, the identifiers are barcodes and the identifier index 52 is a barcode index. However, the identifiers may include an RF identifier (RFID) or any other machine-readable identifier. Additionally, the central database 50 may include patient records 54, supply records 56, caregiver records 58, inventory records 61 and financial records 63. The patient records 54 may include each patient's treatment history, demographic information, orders entered by a physician for treatment of each patient, clinical results and patient tasks and task lists.

The supply records 56 may include the type of supply item including any surgical, medical, diagnostic or other instruments, equipment, clinically related disposable or non-disposable items, such as, for example, instruments such as scalpels, forceps catheters, laparoscopes, joint, bone, dental or other implants, intravenous lines, saline solution, blood serum, syringes, laboratory supplies such as fluid sample cartridges, assay solution or other material, diagnostic material such as X-ray film, protective clothing such as gowns or masks, hospital beds or other clinically related material. The caregiver records 58 may include records of assigned tasks for each caregiver in the system. Inventory records 61 may include information about the clinical supply inventory including quantities, condition, freshness and other data about supplies. Inventory data may further include information regarding the fulfillment, shipment, delivery and other information about the physical purchase and delivery of supply items. Financial records 63 may include financial information for the patient including responsible financial entity, insurance information, Medicaid and Medicare information, patient charges, physician charges, hospital charges, and other financial information regarding the patient's medical treatment to later be used to invoice the responsible financial entity such as the patient, patient's insurance company, Medicaid, Medicare and the like. The orders and other information can be accessed through the caregiver computing device 60 to determine appropriate tasks to be performed on an identified patient.

Figure 5:
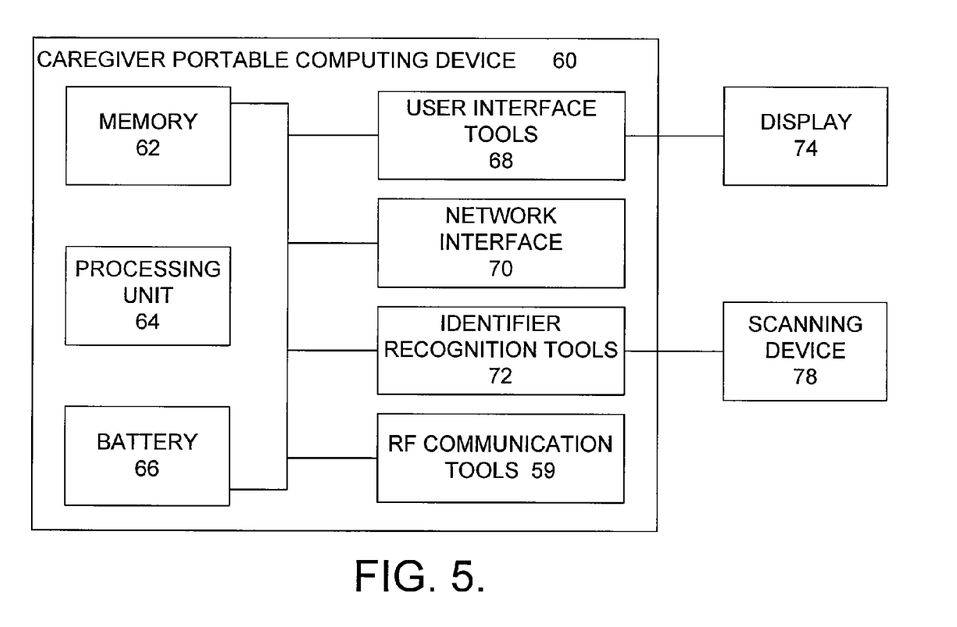
FIG. 5 is a block diagram illustrating a caregiver computing device in accordance with an embodiment of the present invention.

FIG. 5 illustrates an exemplary embodiment of the caregiver computing device 60. The caregiver computing device 60 may include radio frequency (RF) communication tools 59, memory 62, a processing unit 64, a battery 66, user interface tools 68, network interface 70, and identifier recognition tools 72. The user interface tools 68 may advantageously be accessible through a built-in display device 74. The identifier recognition tools 72 may be connected with a scanning device 78 such as an embedded barcode scanner.

In an embodiment of the invention the caregiver computing device 60 is a handheld personal digital assistant (PDA). The PDA puts the information of the central database 50 in the caregiver's hands at the point of care. The PDA recognizes identifiers associated with the patient 2, caregiver 10, supply items 6 and tasks 7. The PDA prompts the caregiver 10 for necessary actions and information during the care-giving process.

The caregiver computing device 60 is used as a verification device and in an embodiment of the invention includes or is connected with a barcode scanner for scanning the patient identifier 4, supply item identifier 8, task identifier 9 and the caregiver identifier 12. Caregivers may be provided with varying access levels. For instance, a physician may be able to enter tasks, but some less skilled caregivers may not be permitted such a high access level. In this instance, the caregiver computing device 60 is capable of verifying access level through the central database 50 and the caregiver identifier 12. If the caregiver is not authorized to complete the task, the system will provide notice to the caregiver and prevent further action related to the task.

The caregiver computing device 60 accesses the central information system 20 through the network interface 70 and prompts caregivers for scheduled tasks, provides alerts to prevent potential errors, facilitates documentation, and allows caregivers to review data before posting it to central database. Real time updates and current access orders are available through the caregiver computing device 60 in real time.

Figure 6:
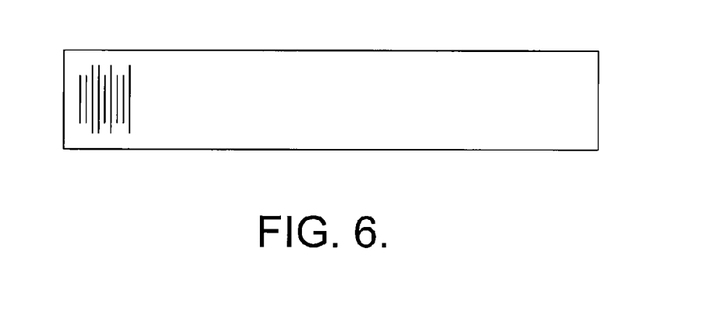
FIG. 6 is a diagram illustrating an identifier in accordance with an embodiment of the present invention.

FIG. 6 illustrates a machine-readable identifier 5, one embodiment of the patient identifier 4. In one embodiment, the patient identifier is in machine-readable form and may be a scannable barcode or RFID. The patient identifier 4 may be in the form of a patient wristband. In one embodiment, the caregiver identifier 12 is in machine-readable form similar to identifier 5. The caregiver identifier 12 may be affixed to a caregiver badge. In embodiments, the supply item identifier 8 also includes a machine-readable identifier as shown. The identifiers associated with the patient, caregiver, and supply item are linked to specific data within the central information system database 50.

Every supply item used in medical treatment of a patient may be labeled with an identifier such as a barcode. This allows supply items that can be tagged with an identifier to be monitored by the system of the invention.

Labeling each component with an identifier provides a physical structure to make supply items and tasks part of the care environment and workflow for providing patient care. If more than one supply item is present, the system is capable of distinguishing them from one another because of the aforementioned identifiers.

Figure 2:
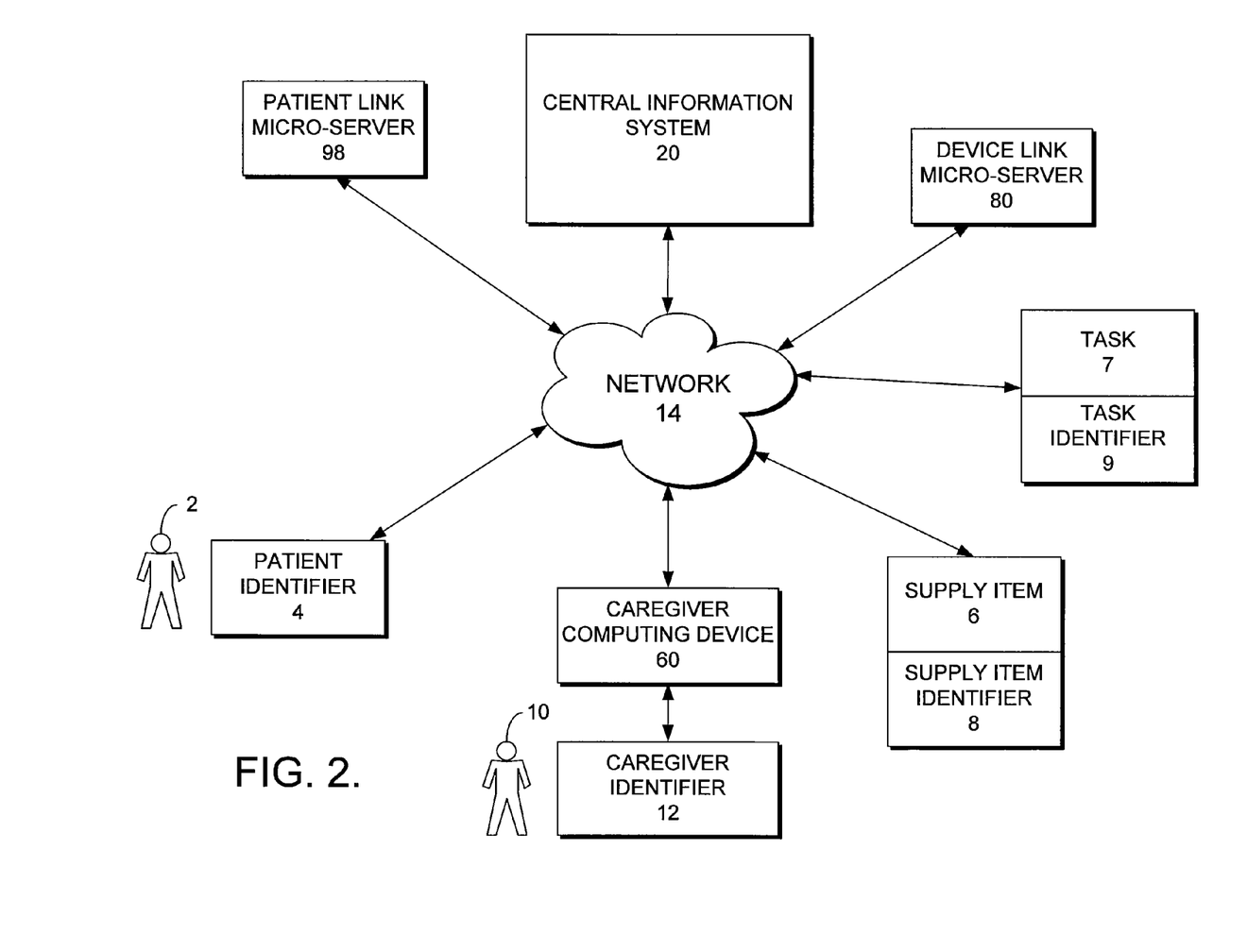
FIG. 2 is a block diagram illustrating components of a system for managing patient care in accordance with an alternative embodiment of the present invention.

In another embodiment of the system of the invention, with reference to FIG. 2, additional components may be included such as a device link micro-server and a patient link micro-server 98. In implementing the system of the invention, these micro-server components 98 and 80 may both be included or either component 98 or 80 may selectively be implemented.

Figure 7:
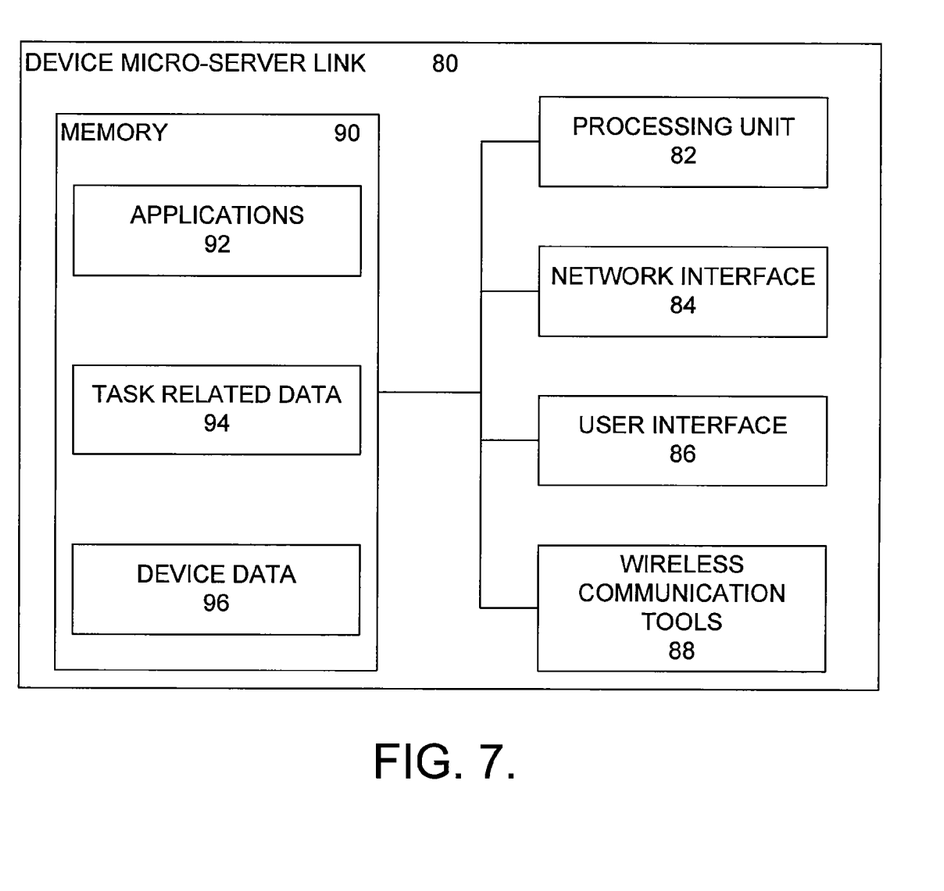
FIG. 7 is a block diagram illustrating a device link micro server in accordance with an embodiment of the present invention.

FIG. 7 illustrates an embodiment of the device link micro-server 80. The device link micro-server 80 may include a processing unit 82, a network interface 84, a user interface 86, and wireless or wired communication tools 88. The device link micro-server 80 may also include a memory 90 including applications 92, task related data 94, and device data 96. The device link micro-server 80 has a device driver within its applications 92 and is capable of determining an appropriate communication protocol for the attached device. The device link micro-server 80 uses standard language protocols to communicate with any device and then converts that information to an appropriate format for user by central information system 20. Although all components are shown as communicating over the network 14, peer-to-peer communication may also be possible.

The patient link micro-server 98 may be substantially identical in structure to the device link micro-server 80 and performs a similar function. However, the application programs running on the two devices may differ. The patient link micro-server 98 and the device link micro-server 80 provide caching or local storage of data. The infrastructure of the micro-server devices 80 and 98 allows retention of data and management at nursing unit level. Data in the micro-servers 80 and 98 may be stored as tagged extensible mark-up language (XML) data.

Both the patient link micro-server 98 and the device link micro-server 80 are capable of functioning as web servers. In one embodiment, the patient link micro-server 98 preferably communicates with the central database 50 via XML but may also support HL7 and could be configured to operate using the Cerner Millennium®, architecture of Cerner Corporation of Kansas City, Mo., or in any appropriate manner in the context of the provided central information system 20. The patient link micro-server 98 stores a snapshot of all information about the associated patient, thus providing back up in case information in the central database 50 becomes inaccessible. The patient link micro-server 98 is capable of functioning as a link between the central database 50 and everything that happens to the patient 2.

The caregiver computing device 60 with the embedded barcode scanner or other identifier recognition mechanism is preferably capable of communication with the device link micro-server 80 and the patient link micro-server 98 with an RF signal. Both devices can communicate over the network 14 with the central information system 20 that supplies primary patient-specific information to the patient link micro-server device 98 while the central information system 20 is available.

The micro-servers 80 and 98 are capable of functioning continuously during downtime of the central information system 20 and have the ability to automatically re-synchronize with the central information system 20 when it becomes available. The patient link micro-server 98 receives updates from the central information system 20 based on design criteria and sends updates to the central information system 20 regarding patient activity and acquired device data. Further, the patient link micro-server 98 stores a record of activity performed at the bedside and any data provided to it by adjacent device link micro-servers 80. In the absence of the central information system 20, the patient link micro-server 98 will continue to check activities against its most current activity list and will queue activity updates and data until the central information system 20 signals its availability to accept those updates.

Figure 8A:
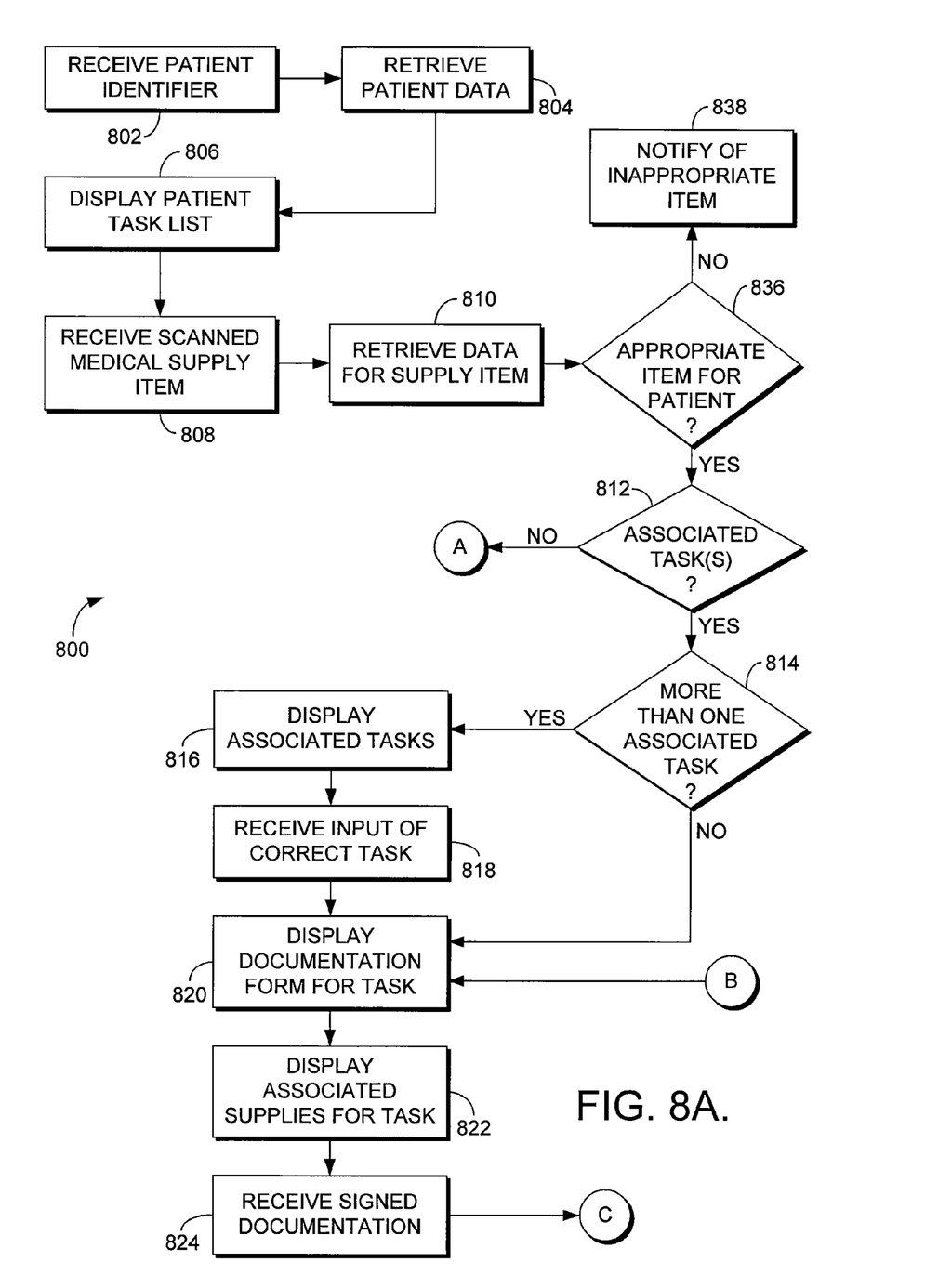
FIG. 8A is a flow chart illustrating a method for displaying associated supplies for a healthcare task in accordance with an embodiment of the present invention.

With reference to FIG. 8A, a method 800 is provided for determining whether a scanned supply item has an associated task for a patient. One or more tasks are created for patients based on orders entered for the patient and dictate a particular course of care. These tasks may be contained within the patient records 54 and the caregiver records 58 of FIG. 4. Tasks are typically generated from orders and specify, with particularity, what is to be done for a patient. Thus, if an order states that a patient is to receive four 20 mg doses of medication X, one dose every three hours beginning at 12:00 pm, four tasks may be generated on the task list associated with the patient: a first task at 12:00 pm, a second task at 3:00 pm, a third task at 6:00 pm, and a fourth task at 9:00 pm, each task indicating that 20 mg of medication X are to be administered. In another example, an order for a medication may require the task of inserting of a supply item, such as a central line according to the system and method described below.

At step 802, the patient is identified by receiving a patient identifier. In one embodiment, a caregiver scans a patient identifier with the caregiver computing device. This step may involve swiping a bar code, RFID or other machine-readable identifier. In one embodiment, the identifier may be located on a patient identification bracelet or a patient link micro server. The patient may also be identified by being input manually.

At step 804, data for the patient is accessed. The patient data may be contained in a patient's electronic medical record. Patient data may include a patient's treatment history, demographic information, orders entered by the physician for treatment of a patient, clinical results, and patient tasks and task lists. Patient data may be obtained from patient records 54 in FIG. 4. At step 808, a medical supply item is identified and input into the system. The scanned medical supply item is input into the system by a caregiver scanning a supply item identifier with the caregiver computing device. Again, this step may involve swiping a bar code, RFID or other machine-readable identifier associated with the supply item. For example, in one embodiment, prior to using the supply item for the patient, the patient is identified and the supply item is scanned by a caregiver computing device.

At step 810, data for the supply item is retrieved. The data for the supply item may include information regarding identification of item, the type of item, size, manufacturer, purpose, associated tasks, and other associated supply items. The identifier obtained from scanning the supply item is used to access the supply record for that item to obtain more data related to the supply item. This information may be contained in supply records 56 as shown in FIG. 4. An exemplary supply record management system may also be utilized with the present invention.

Referring again to FIG. 8A, at step 836 it is determined whether the supply item scanned is appropriate for use with the patient. The patient data retrieved from the patient's electronic medical record is compared with the supply item data retrieved. A supply item may be inappropriate for a patient based on age, weight, allergies, medications being taken, genetic predisposition and/or genetic test results and general state of health. For instance, an adult catheter would not be appropriate for a pediatric patient or a latex supply item may be inappropriate for use on a patient with an allergy to latex. If at step 836 it is determined that the scanned supply item is inappropriate for the patient, a notification or alert of such is generated and sent to the appropriate caregiver at step 838.

If at step 836 it is determined that the supply item is appropriate for the patient, at step 812, it is determined whether there are any tasks on the patient's task list obtained from patient data associated with the scanned supply item. For example, if a catheter supply item is scanned for a patient, it is determined whether any of the tasks on the patient task list are appropriate for use of this item. For example, a catheter may be appropriate for a patient assessment task and a output volume documentation task. While a laparoscope may be appropriate for a medication task.

If it is determined at step 812 that at least one task exists for the scanned supply item, it is determined at step 814 whether more than one associated task would be appropriate for use of the supply item. For example, a catheter may satisfy multiple tasks on a patient's task list such as procedure task and assessment task. If at step 814 it determined that more than one task from the patient's task list is associated with the scanned supply item, at step 816 the multiple tasks associated with the supply item are displayed to a caregiver. At step 818, the selection of the correct task associated with the scanned supply item is received. For example, the caregiver may select from the list of associated tasks the correct task. At step 820, a documentation form for the selected task is displayed.

Figure 10:
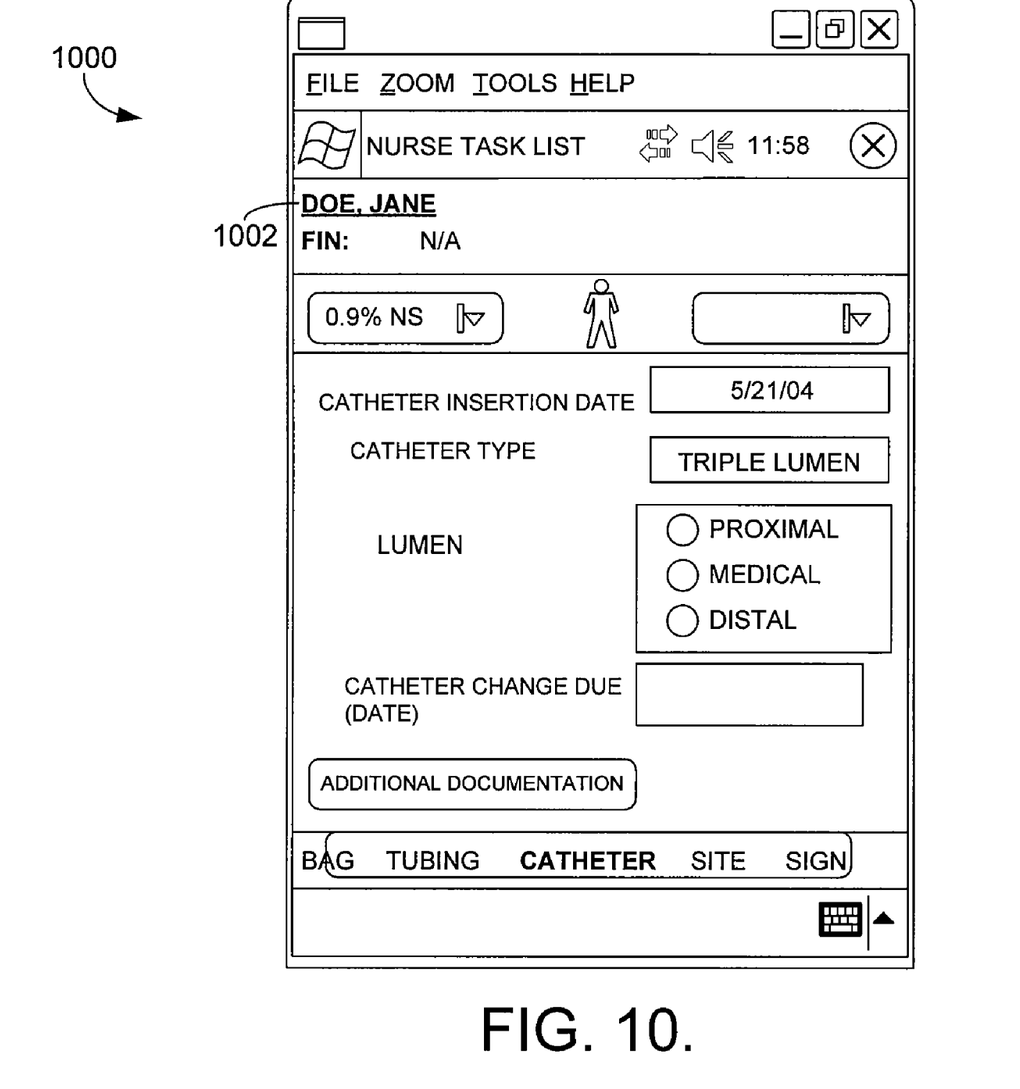
FIG. 10 is an exemplary screen displaying a task documentation form in accordance with an embodiment of the present invention.

If at step 814 it is determined that only one task is associated with the scanned supply item, at step 820 the documentation form for the task is accessed and displayed to the caregiver. Information for the task is documented in the documentation form. An exemplary task documentation form 1000 for a patient 1002 is shown in FIG. 10. The exemplary task documentation form 1000 is for the completion of a catheter insertion task. At step 822, other supplies that are associated with the task for the scanned supply item are displayed to the caregiver so that the caregiver is aware of all the needed supply items for the task. At step 824, signed documentation of the completion of the task is received from the appropriate caregiver.

Figure 8B:
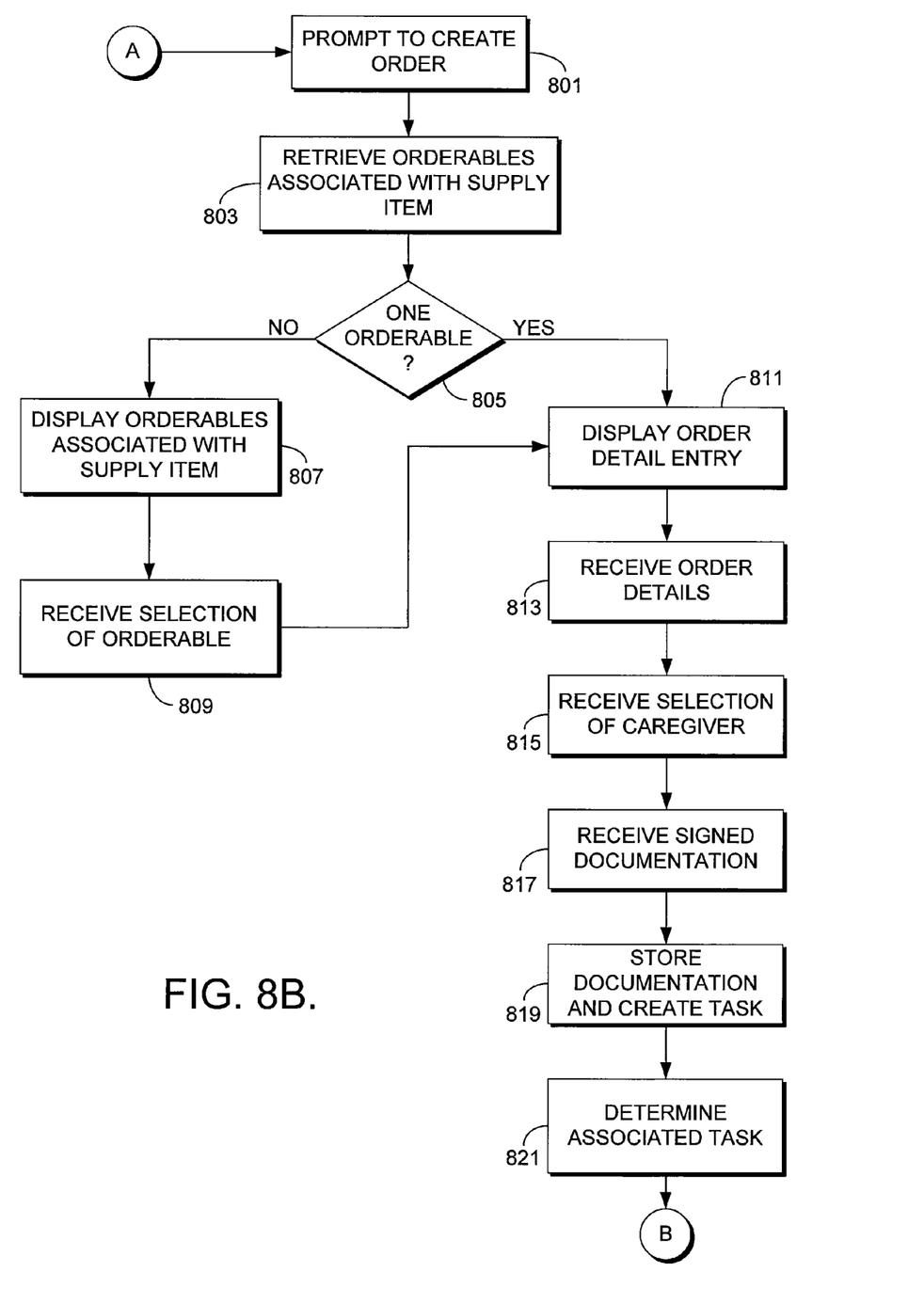
FIG. 8B is a flow chart illustrating a method for receiving orderables associated with a scanned supply item in accordance with an embodiment of the present invention.

Referring back to step 812 of FIG. 8A, if it is determined that no tasks are associated with the scanned supply item, the system proceeds to FIG. 8B. FIG. 8B is a method for creating the appropriate task for the supply item when a task associated with the scanned supply item is not found. An appropriate message at step 801 is displayed and the caregiver is prompted to create a new order for the supply item. If the caregiver would like to create a new order, at step 803 orderables associated with the supply item are retrieved. A computerized table or database having orderables associated with particular supply items is accessed.

At step 805, it is determined whether there are more than one orderables associated with the supply item. If at step 805 it is determined there is only one orderable associated with the scanned supply item, at step 811, the order entry detail screen is displayed. In one embodiment, an order template is displayed on the caregiver portable computing device.

If at step 805 it is determined that more than one orderable is associated with the scanned supply item, at step 807 associated orderables are displayed to a user for selection. At step 809, the selection of the orderable for the supply item is received and at step 811 the appropriate order detail entry screen is displayed. The selection of the orderable may be received through the scanning or an orderable barcode or through a provider selection conversation with the user interface.

A caregiver fills out the form on the order detail screen, signs it and sends the forms to the system. In one embodiment, the forms are sent to the system via the caregiver portable computing device. At step 813, order details are received by the system. The selection of a caregiver is received at step 815 and signed documentation is received at step 817. At step 819 the documentation is stored for the orderable and appropriate tasks for the order are created. This information may be stored in patient records 54 and caregiver records 58 in FIG. 4. For example, if an order for central line placement is placed, tasks for supplies and patient preparation are created. Referring again to FIG. 8B, at step 821, the task associated with the scanned supply item is determined from the one or more tasks created for the order.

Figure 8C:
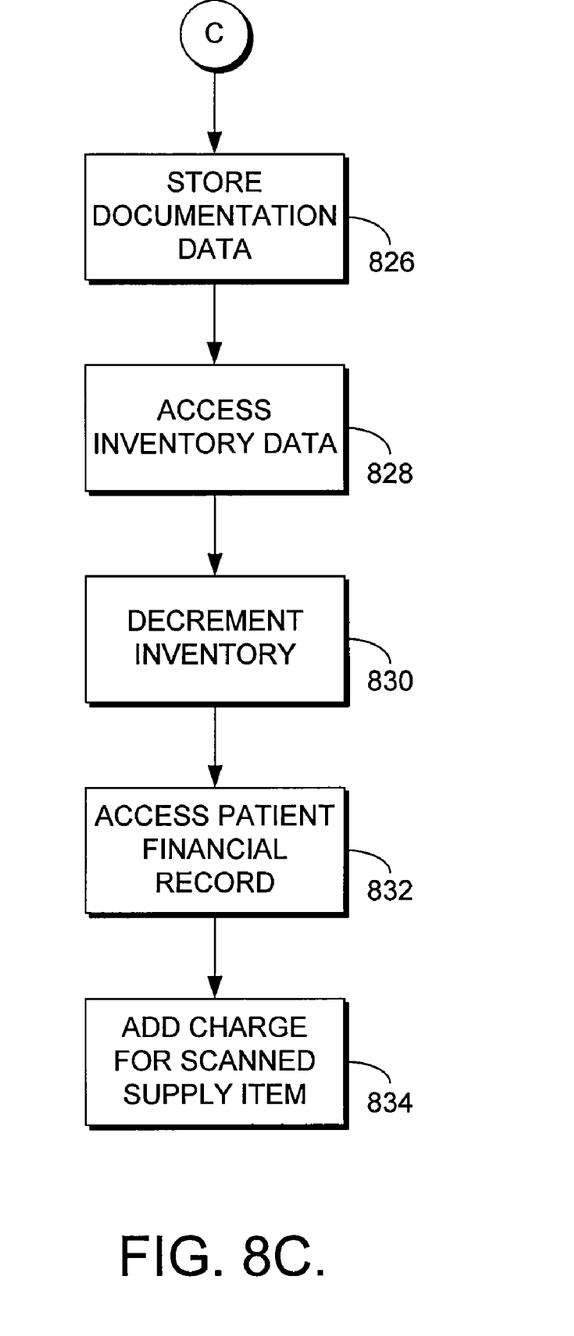
FIG. 8C is a method for decrementing inventory and charging for a scanned supply item in accordance with an embodiment of the present invention.

Referring next to FIG. 8C, after the signed documentation of a completed task is received at step 824 of FIG. 8A, at step 826 of FIG. 8C, the documentation data for the completed task is stored in a computerized database at step 826. At step 828, inventory data is accessed from a computerized database. The inventory data may include the state of clinical supply inventory including quantities, condition, freshness and other data about supplies. Inventory data may further include information regarding the fulfillment, shipment, delivery and other information about the physical purchase and delivery of supply items. At step 830, the inventory amount for the scanned supply item is decremented. In other words, the inventory data is updated to reflect that the quantity of the scanned supply item has decreased with its use for the patient. An exemplary supply management system that may be utilized in conjunction with one or more embodiments of the present invention is Supply Chain Bill Item Master by Cerner Corporation, Kansas City, Mo.

At step 832, a patient's financial record is accessed. The patient's financial record includes financial information for the patient including responsible financial entity, insurance information, Medicaid and Medicare information, patient charges, physician charges, hospital charges, and other financial information regarding the patient's medical treatment to later be used to invoice the responsible financial entity such as the patient, patient's insurance company, Medicaid, Medicare and the like. A charge or indication of use of item is added to the patient's financial record for the scanned supply item used for the patient at step 834. The charge may then be passed along to the party responsible for the patient's healthcare costs or may be used in calculating the appropriate cost for the patient's care. An exemplary financial record management system that may be utilized in conjunction with one or more embodiments of the present invention is BILL OF RESOURCE by Procure offered by Cerner Corporation of Kansas City, Mo.

Figure 9:
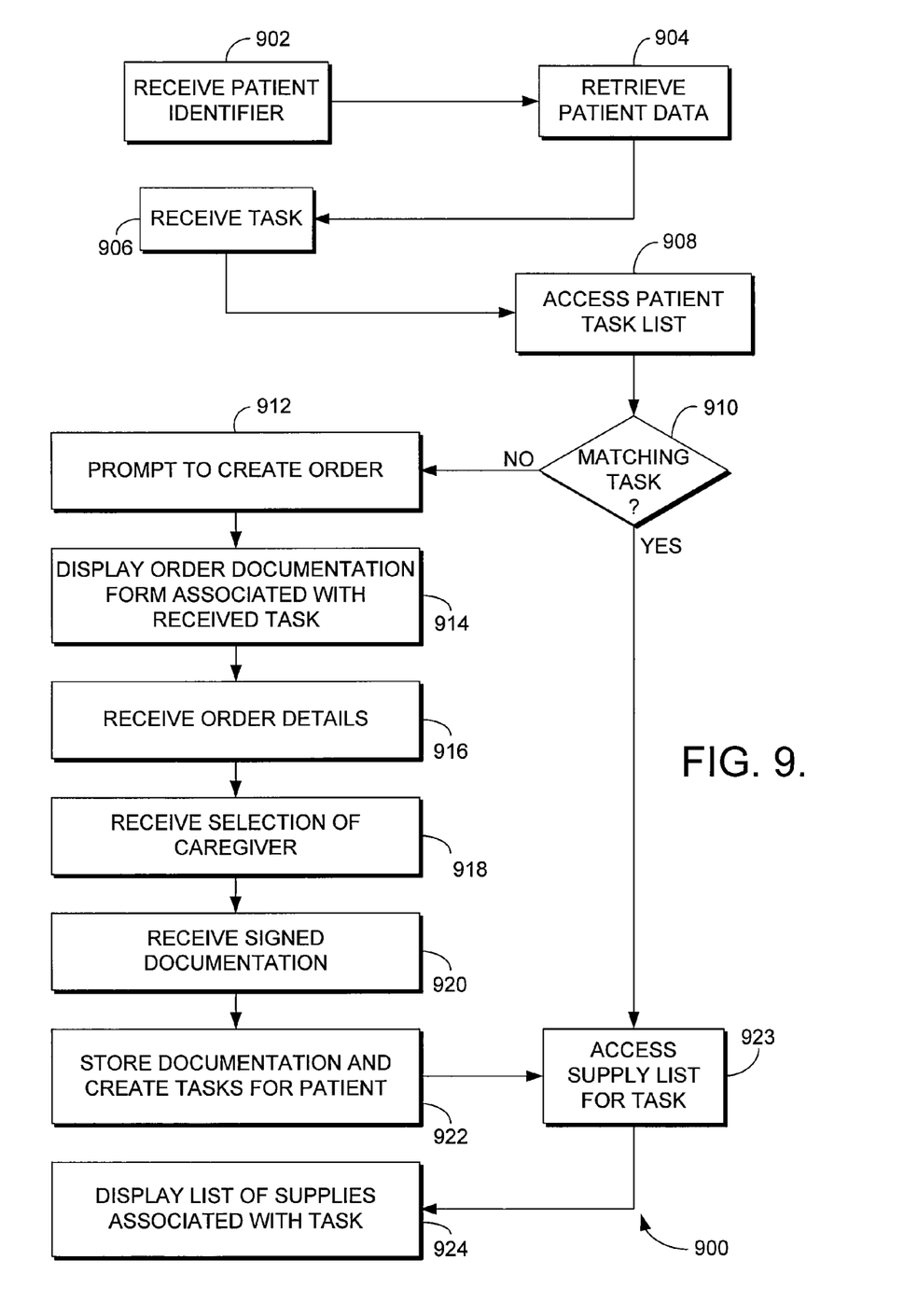
FIG. 9 is a flow chart illustrating a method for displaying a list of supplies associated with the healthcare task in accordance with an embodiment of the present invention.

Referring next to FIG. 9, a method 900 for displaying supply items associated with a task for a patient is shown. At step 902, the patient is identified. In one embodiment, a caregiver scans a patient identifier with the caregiver portable computing device. This step may involve swiping a bar code, RFID or other machine-readable identifier. In one embodiment, the identifier may be located on a patient identification bracelet or a patient link micro server. At step 904, data for the patient identified is retrieved. In one embodiment, the data is retrieved from the patient's electronic medical records. At step 906, the task to complete for the patient is received. The task may be entered into the system by a variety of means. In one embodiment, task identifier, such as a bar code or RFID is scanned and input into the system. In another embodiment, the task is selected or input by a user.

At step 908, the patient's task list is accessed from patient data. It is determined whether the received task matches a task on the patient's task list at step 910. If the received task does not match a task on the patient's task list, at step 912, the user is prompted to create a healthcare order for the patient. At step 914, the appropriate order detail entry screen associated with the task received is displayed to a user.

A caregiver fills out the form on the order detail screen, signs it and sends the form to the system. In one embodiment, the form is sent to the system via the caregiver portable computing device. At step 916, order details are received by the system. The selection of a caregiver is received at step 918 and signed documentation is received at step 920. At step 922 the documentation is stored for the orderable and appropriate tasks for the order are created. At step 923, the supply list for the task received at step 906 is accessed from a computerized database or table. The supply list associated with the task is displayed at step 924.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

The invention claimed is:

1. A method in a computerized healthcare environment for determining whether a supply item is associated with one or more task items for a patient, the method comprising:
receiving a patient identifier to identify a patient;
accessing patient data from the patient's electronic medical record;
receiving a scanned medical supply item identifier identifying a non-pharmaceutical medical supply item;
accessing data for the scanned supply item;
utilizing the supply item data and patient data to determine whether one or more task items for the patient are associated with the scanned supply item, wherein the one or more task items are to be performed by a caregiver;

if no task items for the patient are associated with the scanned supply item, presenting a display that prompts the caregiver to create a healthcare order, for the patient, that uses the scanned supply item; and receiving the healthcare order from the caregiver.

2. The method of claim 1, wherein the patient identifier is a bar code scanned with a portable information device.

3. The method of claim 1, wherein the supply item identifier is a bar code scanned with a portable information device.

4. The method of claim 1, wherein it is determined that more than one task item for the patient is associated with the scanned supply item, displaying the more than one task item for the patient.

5. The method of claim 4, receiving selection of a proper task item for the scanned supply item and displaying a task documentation form for the selected task.

6. The method of claim 1, wherein if it is determined that one or more task items for the patient are not associated with the scanned supply item, determining whether one or more potential orders are associated with the scanned supply item.

7. The method of claim 6, wherein if more than one potential order is associated with the scanned supply item, displaying the orders associated with the scanned supply item.

8. The method of 7, further comprising:

receiving selection of one of the potential orders as the proper order; and displaying the order entry detail screen for the selected order.

9. The method of claim 8, further comprising:

receiving order details for the selected order;

creating appropriate tasks for the selected order; and determining the task associated with the scanned medical supply item.

10. The method of claim 6, wherein if only one order is associated with the scanned supply item, displaying the order entry detail screen for the one order.

11. The method of claim 10, further comprising:

receiving order details for the associated order;

creating appropriate tasks for the associated order; and determining the task associated with the scanned medical supply item.

12. The method of claim 1, wherein if it is determined that one task for the patient is associated with the scanned supply item, displaying a task documentation for the task.

13. The method of claim 12, further comprising:

determining whether additional supply items are needed for completion of the task.

14. The method of claim 13, further comprising:

displaying the additional supply items needed for completion of the task.

15. A computerized system for determining whether one or more supply items is associated with one or more task items for a patient, the system comprising:

a central information system containing patient data and supply item data;

a patient identifier linking a patient to patient data in the central information system;

a supply item identifier linking the non-pharmaceutical medical supply item to supply item data in the central information system; and a portable information device for:

(1) collecting the patient identifier and the supply item identifier, (2) communicating with the central information system to access the patient data and supply item data, (3) receiving at least two tasks associated with the non-pharmaceutical medical supply item for a caregiver to complete using the non-pharmaceutical medical supply item, (4) presenting the at least two tasks on a display of the portable information device, (5) receiving a selection from the caregiver of one of the at least two tasks to complete with the non-pharmaceutical medical supply item, and (6) presenting a documentation on the screen, wherein the documentation is configured to receive a signature from the caregiver that indicates completion of the one of the at least two tasks.

16. The system of claim 15, wherein the patient identifier and supply item identifier are bar codes scanned with the portable information device.

17. The system of claim 15, wherein the patient data includes a patient task list.

18. One or more computer-readable media having computer-executable instructions embodied thereon for performing a method for retrieving and transmitting patient data in a computerized environment, the method comprising:

retrieving a patient identifier with a portable information device, wherein the patient identifier identifies a patient;

retrieving a supply item identifier with a portable information device, wherein the supply item identifier identifies a non-pharmaceutical medical supply item;

transmitting the patient identifier and the supply item identifier to a central information system;

determining two or more tasks to be completed by a caregiver that are associated with the non-pharmaceutical medical supply item, wherein the two or more tasks are based on an order;

presenting, on a display device, the two or more tasks to the caregiver;

receiving a selection, from the caregiver, of at least one of the two or more tasks;

based on the selection, presenting, on the display device, a documentation screen for the at least one of the two or more tasks; and receiving an electronic signature, from the caregiver, indicating completion of the at least of the two or more tasks.

19. The media of claim 18, wherein the current patient related information includes one or more task items associated with the supply item.

20. The media of claim 18, wherein the patient identifier is a bar code scanned with a portable information device.

21. The media of claim 18, wherein the supply item identifier is a bar code scanned with a portable information device.

22. The media of claim 18, wherein the current patient related information includes that no task items for the patient are associated with the supply item.

* * * * *

UNITED STATES PATENT AND TRADEMARK OFFICE
CERTIFICATE OF CORRECTION

PATENT NO. : 7,690,558 B2 Page 1 of 1
APPLICATION NO. : 11/424378
DATED : April 6, 2010
INVENTOR(S) : Charles S. Fox, Jr. et al.

It is certified that error appears in the above-identified patent and that said Letters Patent is hereby corrected as shown below:

Title Page, Item (73) Assignee: delete "CEMER" and replace with "CERNER"

Signed and Sealed this

Twentieth Day of July, 2010

David J. Kappos
*Director of the United States Patent and Trademark Office*